United States Patent [19]

Mittermeier

[11] Patent Number: 5,092,870
[45] Date of Patent: Mar. 3, 1992

[54] SPACER CLIP FOR USE WITH A BIOPSY APPARATUS

[75] Inventor: Anton Mittermeier, Skokie, Ill.
[73] Assignee: M3 Systems, Inc., Northbrook, Ill.
[21] Appl. No.: 692,007
[22] Filed: Apr. 26, 1991
[51] Int. Cl.⁵ ............................................. A61B 10/00
[52] U.S. Cl. ................................. 606/151; 128/749; 24/457
[58] Field of Search ................... 128/749, 751–754; 606/151, 157, 167, 170–172, 185; 24/457, 570, 571

[56] References Cited

U.S. PATENT DOCUMENTS

| | | | |
|---|---|---|---|
| 3,629,912 | 12/1971 | Klopp | 24/457 |
| 4,519,392 | 5/1985 | Lingua | 606/151 |
| 4,699,154 | 10/1987 | Lindgren | 128/754 |
| 4,716,886 | 1/1988 | Schulman et al. | 606/167 |
| 4,890,626 | 1/1990 | Wang | 128/752 |

FOREIGN PATENT DOCUMENTS 2036725  1/1979  Fed. Rep. of Germany ...... 606/157

*Primary Examiner*—Max Hindenburg
*Attorney, Agent, or Firm*—Dick and Harris

[57] ABSTRACT

A spacer clip apparatus, for use with a biopsy needle, having first inner and second outer needle components, is provided. The first inner and second outer needles are provided with first and second handles, respectively. The spacer clip apparatus includes a pair of splines, which extend parallel to and in opposite directions away from opposite sides of a stem. Hook members placed at the ends of the splines, remote from the stem, frictionally engage the respective first and second handles of the first inner and second outer needles.

11 Claims, 1 Drawing Sheet

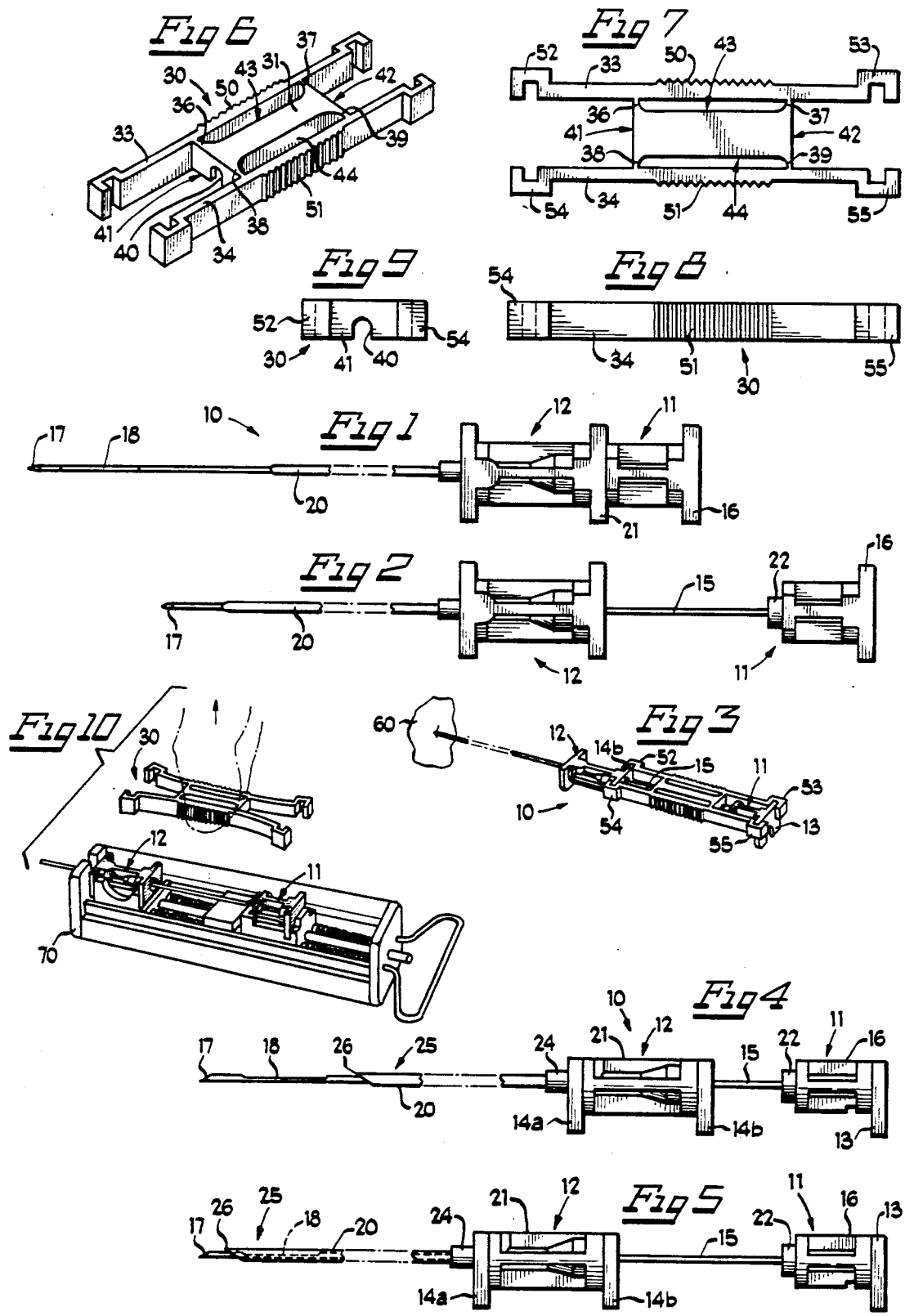

SPACER CLIP FOR USE WITH A BIOPSY APPARATUS

BACKGROUND OF THE INVENTION

The present invention relates to tissue sampling devices known as biopsy needles, and in particular, to clips for use in manipulating and transporting such biopsy needles.

A typical biopsy needle for use in obtaining tissue samples is composed of two parts, a first inner needle and a second outer needle. The first inner needle consists of a solid shaft, having a first handle disposed at one end. A cutting point, to facilitate insertion of the needle into the tissue to be sampled, is located at the opposite end of the shaft from the first handle. Positioned just away from the cutting point, toward the first handle, is the tissue holding region, which is in the form of a cut out region in the shaft.

The second outer needle is made up of a hollow shaft, also at one end of which is disposed a second handle. A passageway extends through the second handle, connected to the hollow shaft, to enable the solid shaft of the first inner needle to be inserted into the passageway and into and through the hollow shaft of the second outer needle.

The first inner needle is greater in length than the entire second outer needle structure. When the first and second handles are placed in a particular spaced position, the hollow shaft of the second outer needle covers the tissue holding region. The tissue holding region may be exposed by inserting the first inner needle further into the second outer needle, bringing the first and second handles closer together. To obtain a tissue sample, the biopsy needle is inserted into a patient, into the tissue to be sampled, with the first inner and second outer needles relatively positioned so that the tissue holding region is covered. The tissue holding region then is exposed, by the operator holding the second handle of the second outer needle motionless while thrusting the first inner needle forward. A portion of the tissue moves into the tissue holding region.

The second outer needle, which also has a cutting point disposed at the end of the hollow shaft opposite the second handle, is then thrust forward, relative to the now-held motionless first inner needle, to cut off the tissue sample from the rest of the tissue, and cover the tissue sample. The angled cutting point of the second outer needle serves to sever the tissue sample. Accordingly, the first inner and second outer needles must be placed in a particular rotational orientation, with respect to one another, prior to insertion, so as to preclude unnecessary manipulation of the needles while in the patient. Specifically, the leading tip of the angled point of the second outer needle must be positioned so as to pass over the tissue holding region. It is therefore desirable to provide a means for retaining the needles in such particular rotational orientation, prior to insertion, and as well during removal.

When the tissue cutting step is accomplished, then the first inner and second outer needles have been brought back to the same relative positions which they occupied prior to initial insertion of the biopsy needle into the patient. To prevent loss or contamination of the tissue sample, the first inner and second outer needles must be removed in this configuration from the patient as well. It is desirable, therefore, to provide a means for maintaining the needles in the appropriate relative positions during removal.

As the configuration of the first inner and second outer needles, which is appropriate for initial insertion, and final removal from the patient, requires that the first and second handles be held spaced apart, the manipulation of such a biopsy needle requires considerable dexterity and concentration on the part of the operator. The concentration necessary to maintain the proper spacing may detract from the concentration necessary to make insertion and removal of the biopsy needle as painless as possible for the patient.

In an alternative usage of a biopsy needle, such a needle is deployed with an automatic device which accomplishes the intermediate steps between initial insertion and final removal. Such an automatic tissue sampling machine is disclosed in U.S. Pat. No. 4,699,154 issued to Lindgren. Prior to loading the biopsy needle into the tissue sampling machine, in the required configuration, the first inner and second outer needles must still be maintained in such position, to facilitate mounting of the biopsy needle in the tissue sampling machine. Further, once removed from the tissue sampling machine, the first inner and second outer needles must still be maintained in the original configuration, to keep the tissue holding region covered and prevent loss or contamination of the tissue sample.

It is desirable therefore to provide a means for maintaining the first inner and second outer needles of a biopsy needle in a predetermined spaced configuration during initial manual insertion and removal.

Still another object of the invention is to provide a means for preventing rotation of the first inner and second outer needles with respect to one another, once the needles have been positioned in a predetermined desired relative orientation.

It is a further object of the invention to provide a means for maintaining the first inner and second outer needles of a biopsy needle in the desired configuration for preventing loss or contamination of the obtained tissue sample during transportation of the biopsy needle for deposit of the tissue sample.

Yet another object of the invention is to provide a means for maintaining the first inner and second outer needles of a biopsy needle in the appropriate configuration for loading into a tissue sampling machine, and upon removal after use thereof.

These and other objects of the invention will become apparent in light of the present Specification, Drawings and claims.

SUMMARY OF THE INVENTION

The present invention is directed to a spacer clip, in particular, a spacer clip for use with a biopsy needle. Such a biopsy needle is of the kind which has a first inner needle having shaft member and two ends, a first handle at one end, a cutting point at the other end, and a tissue holding region positioned between the cutting point and the first handle. Such a needle also has a second outer needle having a hollow shaft, and two ends with a cutting point at one end and a second handle at the other end. The second handle has a passageway therethrough for reciprocation of the first inner needle to enable the first inner needle to be inserted into the second outer needle.

The shaft of the first inner needle has a length greater than the overall length of the second outer needle, so that the cutting point of the first inner needle can extend beyond the cutting point of the second outer needle. The first inner and second outer needles are positionable into at least two configurations, the first of which positions the tissue holding region outwardly beyond the cutting point of the second outer needle, and the second of which positions the hollow shaft of the second outer needle immediately about the tissue holding region so as to surround and enclose same. The spacer clip is removably engageable with the first and second handles of the first and second needles to maintain each of the needles in the second of the two configurations, to retain tissue sampled within the tissue holding region, to preclude loss or contamination of the retrieved tissue sample, and/or alternatively configuring the first and second handles of the first and second needles in position for loading into a tissue sampling machine. The spacer clip apparatus alternatively maintains and releases the first handle of the first inner needle and the second handle of the second outer needle in and from a predetermined axially spaced relationship, in a facilitated manner.

The spacer clip apparatus comprises support body means, handle receipt means positioned along the support body means for engaging the first and second handles of the first inner and second outer needles, respectively, to maintain the first and second handles of the first inner and second outer needles in the second of the two configurations, positioning the hollow shaft of the second outer needle immediately about the tissue holding region of the first inner needle to surround and end enclose same to retain tissue sampled therewithin, by positioning the first handle of the first inner needle and the second handle of the second outer needle in the predetermined, axially spaced relationship, as dictated by the location of the handle receipt means along the support body means, for substantially simultaneously disengaging the first and second handles of the first inner and second outer needles.

In the preferred embodiment of the invention, the support body means is a stem, having a longitudinal axis, with two opposed sides of the stem extending substantially parallel to the longitudinal axis. Two opposed ends extend substantially perpendicular to the longitudinal axis.

The handle receipt means comprise first and second pairs of opposed hook members, which operably emanate from respective ends of the stem. Each of the hook members of the first and second pairs of opposed hook members is disposed at a predetermined laterally spaced relationship to the other of the opposed hook members, to frictionally engage therebetween the first and second handles of the first inner and second outer needles, respectively.

The handle receipt means further comprise means for substantially simultaneously deflecting the hook members of each of the first and second pairs of opposed hook members, from their predetermined laterally spaced relationship, and further comprises at least one spline, operably affixed to one of the opposed sides of the stem. At least one spline extends substantially parallel to the longitudinal axis, in opposite directions beyond and away from the ends of the stem, and has two ends. At least one hook member of each of the first and second pairs of opposed hook members is operably disposed on each spline end so that each of the first and second pairs of opposed hook members are arranged in the predetermined laterally spaced relationship.

The one spline is affixed to the stem by webs extending outwardly from the stem at its ends, substantially perpendicular to the longitudinal axis of the stem, so as to hold the spline in substantially parallel, spaced relationship to the stem. The spline is further fabricated of a resistively flexible material which will bend under the exertion of manual pressure, inwardly toward the stem, such that upon the exertion of squeezing pressure, inwardly toward the stem by an operator upon the at least one spline, between the webs, the ends of the one spline will deflect outwardly laterally away from the stem, facilitating release of, or fit onto, one of the respective handles of the first inner and second outer needles.

In the preferred embodiment of the invention, two splines, are provided, one spline operably affixed to each of the opposed sides of the stem, the two splines each extending substantially parallel to the longitudinal axis, in opposite directions beyond and away from the ends of the stem, and each of the two splines has two ends. One hook member of each of the first and second pairs of opposed hook members is operably disposed on each spline end so that each of the first and second pairs of opposed hook members are arranged in the predetermined laterally spaced relationship.

Furthermore, each of the two splines is affixed to the stem by webs extending outwardly from the stem at its ends, substantially perpendicular to the longitudinal axis of the stem, so as to hold the splines in substantially parallel, spaced relationship to the stem, and each of the splines is fabricated of a resistively flexible material which will bend under the exertion of manual pressure, inwardly toward the stem, such that upon the exertion of squeezing pressure, inwardly toward the stem by an operator upon the splines, between the webs, the ends of splines will deflect outwardly laterally away from the stem, facilitating release of, or fit onto, the first and second handles of the first inner and second outer needles, respectively.

Means may be provided for facilitating grasping of the spacer clip. Specifically, the splines may be provided with sides facing outwardly away from the stem, and the means for facilitating grasping of the spacer clip are a plurality of reeded ridges operably disposed on the outwardly facing sides of the splines. The plurality of reeded ridges may be disposed on the outwardly facing sides of the splines in parallel, spaced relation to each other, each reeded ridge extending in a plane disposed substantially perpendicular to the longitudinal axis of the stem.

BRIEF DESCRIPTION OF THE DRAWINGS

FIG. 1 is a bottom plan view of a typical biopsy needle having the tissue holding region exposed;

FIG. 2 is a bottom plan view of the needle of FIG. 1, showing the hollow shaft of the second outer needle covering the tissue holding region;

FIG. 3 is a perspective view of a needle, with the spacer clip apparatus in place, when manually inserted;

FIG. 4 is a side elevation of the biopsy needle according to FIG. 1, with the inner and outer needles spaced apart in the requisite insertion and removal configuration;

FIG. 5 is a side elevation of the needle of FIG. 2;

FIG. 6 is a perspective view showing use of the spacer clip apparatus to install a needle into a tissue sampling machine;

FIG. 7 is a top plan view of the spacer clip apparatus according to FIG. 6;

FIG. 8 is a side elevation of the spacer clip apparatus according to FIG. 6;

FIG. 9 is an end elevation of the spacer clip apparatus according to FIG. 6; and FIG. 10 is a perspective view of a tissue sampling machine and needle, showing manipulation of the spacer clip apparatus.

DETAILED DESCRIPTION OF THE DRAWINGS

While the present invention is susceptible of embodiment in many different forms, there is shown in the drawings and will be described in detail, a specific embodiment, with the understanding that the present disclosure is to be considered as an exemplification of the principles of the invention, and is not intended to limit the invention to the embodiment illustrated.

A typical needle for use in obtaining biopsy samples is illustrated in FIGS. 1-5. Biopsy needle 10 is composed of two parts, first inner needle 11 and second outer needle 12. Inner needle 11 consists of a solid shaft 15 which is embedded in first handle 16. Angled point 17 is positioned at the opposite end of shaft 15 from first handle 16, to facilitate insertion of the needle into the tissue to be sampled. Just removed from point 17, tissue holding region 18 is cut out from shaft 15, as illustrated in FIG. 4. When biopsy needle 10 is inserted into a tissue to be sampled, and tissue holding region 18 is exposed, as described hereinafter, a portion of the tissue moves into tissue holding region 18, and is cut off and retained there to become the tissue for the desired sample.

Shaft 15 is freely insertingly received by hollow shaft 20 of second outer needle 12, which is embedded in second handle 21. An aperture (not shown) extends through the length of second handle 21. As shown, first handle 16 may have projection 22 extending along shaft 15. In such case, an enlarged portion of the aperture in second handle 21 is provided to receive projection 22, with a slightly forced fit. When handles 16 and 21 are thus brought together, as shown in FIG. 1, first inner needle 11 and second outer needle 12 are held together, which facilitates transport of biopsy needle 10, prior to use. Handles 16 and 21 are additionally configured to be asymmetrical, particularly with tabs 13, 14a and 14b, which have portions projecting perpendicularly from handles 16 and 21, respectively. As the length of shaft 15 exceeds the combined length of hollow shaft 20 and second handle 21, point 17, at substantially all times during normal use, is exposed. Accordingly, projection 24 is provided on the shaft side of second handle 21, onto which a protective tube (not shown) may be thrust, to sheath shaft 15 and point 17, to both protect shaft 15 and point 17 from damage, and to protect persons handling biopsy needle 10 from inadvertent injury or contact with point 17. The foregoing description is merely of a typical biopsy needle, and accordingly the particular contours, proportions and configurations may vary from one manufacturer to another. However, the principles of the spacer clip apparatus of the present invention are applicable to all. The operation of biopsy needle 10, to obtain and retrieve a tissue sample, is as follows. When point 17 is inserted into a tissue, first inner needle 11 and second outer needle 12 must be in the configuration shown in FIG. 5, that is, with second outer needle 12 moved forward relative to first inner needle 11, so that hollow shaft 20 covers tissue holding region 18 of shaft 15, but point 17 remains forwardmost and exposed.

Once first inner needle 11 and second outer needle 12 have been inserted into the tissue, first inner needle 11 is moved forward, with respect to second outer needle 12, further into the particular region of the tissue from which a sample is to be retrieved. During this step, second outer needle 12 is to be maintained as motionless as possible, with respect to the patient and the tissue, for accuracy and the comfort of the patient.

As point 17 of first inner needle 11 proceeds further into the tissue, tissue holding region 18 becomes exposed. As the tissue is not a rigid tissue, a portion of the tissue "flows" to fill in, at least partially, tissue holding region 18. To retrieve and remove the sample, second outer needle 12 is then moved forward, relative to first inner needle 11, which must at this time, in turn, be held motionless relative to the patient and the tissue.

As illustrated in FIGS. 4 and 5, hollow shaft 20 also is provided with point 25, which is also angled so that the extreme tip 26 of point 25 is positioned, when first inner needle 11 and second outer needle 12 are aligned, on the side of shaft 15 in which tissue holding region 18 is formed. Proper alignment of first inner needle 11 and second outer needle 12 is attained when the projecting portions of tabs 13, 14a and 14b are aligned. Accordingly, as second outer needle 12 is moved forward relative to first inner needle 11, extreme tip 26 cuts the tissue to leave a portion of the tissue within tissue holding region 18. As second outer needle 12 continues to move forward, the tissue sample, and tissue holding region 18 are covered. At this point, first inner needle 11 and second outer needle 12 have resumed the relative positions indicated by FIG. 5, and must be withdrawn from the patient together in that position, in order to prevent the tissue sample from being dislodged or contaminated by other tissue.

In order to assist in the operation and manipulation of such a biopsy needle, the needle spacer clip apparatus of the present invention is shown, in FIGS. 6-10. Spacer clip apparatus 30 includes stem 31 and splines 33 and 34, which are joined to stem 31 by webs 36 and 37, and 38 and 39, respectively. Stem 31 may be either a substantially solid rectangular member, or as in the preferred embodiment, a shell having ends 41 and 42, sides 43 and 44, and top 45. Cutouts are formed in the ends of stem 31, for example, cutout 46, to accommodate shaft 15 of first inner needle 11, as will be shown hereinafter. If, in an alternative embodiment, stem 31 is to be fabricated as a solid block of material (not shown), a continuous passage extending the length of stem 31 may be provided.

To facilitate grasping and manipulation of clip 30, the outward-facing sides of splines 33 and 34 are provided with reeded portions 50 and 51, respectively. First pair of hook members 52 and 54, and second pair of hook members 53 and 55 are formed at the ends of splines 33 and 34, and are configured to fit around the edges of tabs 14b and 13, respectively. Specifically, clip 31 is appropriately dimensioned so as to fit upon the upper, non-extending portions of tabs 13 and 14b, when first inner needle 11 and second outer needle 12 are in the configuration shown in FIG. 5, which has been previously described as the configuration appropriate for initial insertion and final removal of biopsy needle 10. Although hook members 52 -55 are shown shaped to accept the substantially rectangular edges of tabs 13 and 14b, they may, of course, be configured as necessary to accommodate varying contours of biopsy needles of different manufacture, so long as a releasable friction fit is established, without departing from the scope of the invention.

The use and operation of clip 30 is accomplished in the manner described hereinafter. Firstly, first inner needle 11 and second outer needle 12 must be arranged in the appropriate spaced relation, with handles 16 and 21 aligned, so that second outer shaft 20 covers tissue holding region 18. Once first inner needle and second outer needle 12 are in the requisite position and orientation, spacer clip apparatus 30 is then fitted onto biopsy needle 10. Spacer clip apparatus 30 may be fitted onto either the projecting or non-projecting portions of table 13 and 14b, if biopsy needle 10 is to be used manually, although if a tissue sampling machine, such as tissue sampling machine 70, shown in FIG. 10, is to be used, then spacer clip apparatus 30 must be fitted to the non-projecting portions of tabs 13 and 14b, as the projecting portions typically are configured to cooperate with the mechanism of the tissue sampling machine. For the present disclosure, the latter configuration is shown for both manual and automatic applications.

First pair of hook members 52 and 54 grasp the non-projecting side of tab 14b while second pair of hook members 53 and 55 grasp the non-projecting side of tab 13. Shaft 15, which would otherwise prevent the positioning of clip 30, is accommodated by the cutouts in stem 31, such as cutout 40, previously described.

When clip 30 is in place on biopsy needle 10, friction holds clip 30 in place. To facilitate removal of clip 30, one simply squeezes clip 30 with fingertip pressure at reeded portions 50 and 51, as seen in FIG. 10, which causes the ends of splines 33 and 34 to bow outward, and the centers of splines 33 and 34 are pressed toward stem 31 and each other, substantially simultaneously releasing tabs 13 and 14b of handles 16 and 21.

In an alternative embodiment of the invention, one of splines 33 and 34, rather than being joined to stem 31 by webs, may instead emanate directly from the ends 41 and 42 of stem 31. In this embodiment (not shown), when clip 30 is squeezed, the ends of the remaining spline attached by webs, bow outwards. Such an embodiment may be desirable when a clip having greater stiffness and grasping capacity is desired.

The present invention is also useful in the embodiment of a tissue sampling machine for a biopsy needle, such as tissue sampling machine 70, shown in FIG. 10. Such a tissue sampling machine accomplishes the intermediate steps of driving the first inner needle forward while maintaining the second outer needle motionless, and then further driving forward the second outer needle, to cut off and cover the tissue sample in the tissue holding region. The operator would then be freed to focus attention on the initial insertion and rapid removal of biopsy needle 10, as a unit, so as to shorten the duration of the procedure and lessen the discomfort of the patient.

In such an embodiment, clip 30 is used to hold biopsy needle 10, while positioning same within tissue sampling machine 70. Tissue sampling machine 70 is then manually held to accomplish insertion of biopsy needle 10 into mass 75. Once biopsy needle 10 has been inserted, tissue sampling machine 70 is actuated, and withdrawn. During removal of biopsy needle 10, clip 30 is used to "lock" first inner needle 11 and second outer needle 12 into the desired configuration, to prevent relative rotation or axial movement of first inner needle 11 and second outer needle 12, and preclude loss of the tissue sample.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A spacer clip apparatus, for use with a biopsy needle of the kind including a first inner needle having a shaft member and two ends, a first handle disposed at one end of the shaft member, a cutting point disposed at the other end of the shaft member, and a tissue holding region positioned between the cutting point and the first handle, and a second outer needle having a hollow shaft and two ends, the second outer needle also having a cutting point disposed at one end of the hollow shaft, a second handle with a passageway arranged therethrough for reciprocation of said first inner needle, said second handle disposed at the other end of the hollow shaft, to enable the first inner needle to be inserted into the second outer needle, the shaft member of the first inner needle having a length greater than the overall length of the second outer needle to enable the cutting point of the first inner needle to extend beyond the cutting point of the second outer needle, said first inner and second outer needles being positionable into at least two configurations, a first of said configurations positioning the tissue holding region of said first inner needle outwardly beyond the cutting point of the second outer needle, and a second of said configurations positioning the hollow shaft of the second outer needle immediately about the tissue holding region of said first inner needle so as to surround and enclose same, said spacer clip apparatus being configured to be removably engageable with the first and second handles of the first inner and second outer needles, respectively, to maintain each of said needles in the second of said two configurations in which said hollow shaft of said second outer needle surrounds and encloses said tissue holding region of said first inner needle, to retain tissue being sampled therewithin said tissue holding region, to preclude loss or contamination of said retrieved tissue sample, and/or alternatively configuring said first and second handles of said first and second needles in position for facilitated loading into a tissue sampling machine, said spacer clip apparatus maintaining and alternatively releasing the first handle of the first inner needle and the second handle of the second outer needle in and from a predetermined axially spaced relationship respectively, in a facilitated manner, the spacer clip apparatus comprising:

support body means;

handle receipt means positioned along said support body means for engaging the first and second handles of said first inner and second outer needles, respectively, to maintain the first and second handles of the first inner and second outer needles in said second of said configurations positioning the hollow shaft of the second outer needle immediately about the tissue holding region of said first inner needle so as to surround and enclose same to retain tissue being sampled therewithin said tissue holding region, through positioning of said first handle of the first inner needle and the second handle of the second outer needle in said predetermined, axially spaced relationship, as dictated by the location of said handle receipt means along the support body means; and handle disengagement means operably connected to said support means and said handle receipt means for substantially simultaneously disengaging, in a facilitated manner said first and second handles of said first inner and second outer needles respectively.

2. The spacer clip apparatus according to claim 1 wherein said support body means comprises:

a stem, having a longitudinal axis, two opposed sides of the stem extending substantially parallel to the longitudinal axis, and two opposed ends extending substantially perpendicular to the longitudinal axis.

3. The spacer clip apparatus according to claim 2 wherein said handle receipt means for engaging the first handle of the first inner needle and the second handle of the second outer needle comprises:

first and second pairs of opposed hook members operably emanating from opposed ends of the stem, each of the opposed hook members of each of said first and second pairs disposed at a predetermined laterally spaced relationship to the other of the opposed hook members, to frictionally engage therebetween the first and second handles of the first inner and second outer needles, respectively.

4. The spacer clip apparatus according to claim 3 wherein said handle disengagement means for substantially simultaneously disengaging the first handle of the first inner needle and the second handle of the second outer needle comprises:

means for substantially simultaneously deflecting the hook members of each of the first and second pairs of opposed hook members, from their predetermined laterally spaced relationships.

5. The spacer clip apparatus according to claim 4 wherein said means for substantially simultaneously deflecting the hook members of each of the first and second pairs of opposed hook members, from their predetermined lateral spaced relationship comprises:

at least one spline operably affixed to one of the opposed sides of the stem, the at least one spline extending substantially parallel to the longitudinal axis, in opposite directions beyond and away from the ends of the stem, the at least one spline having two ends; and at least one hook member of each of the first and second pairs of opposed hook members operably disposed on each spline end whereby each of the first and second pairs of opposed hook members is arranged in the predetermined laterally spaced relationship.

6. The spacer clip apparatus according to claim 5 wherein the means for substantially simultaneously deflecting the hook members of each of the first and second pairs of opposed hook members, from their predetermined lateral spaced relationship further comprises:

the at least one spline being affixed to the stem by webs extending outwardly from the stem at its ends, substantially perpendicular to the longitudinal axis of the stem, so as to hold the spline in substantially parallel spaced relationship to the stem; and the at least one spline being fabricated of a resistively flexible material which will bend under the exertion of manual pressure, directed inwardly toward the stem, such that upon the exertion of squeezing pressure by an operator upon the at least one spline, between the webs, the ends of the at least one spline will deflect outwardly laterally away from the stem, facilitating release of, or fit onto, one of the respective handles of the first inner and second outer needles.

7. The spacer clip apparatus according to claim 5 wherein the means for substantially simultaneously deflecting the hook members of each of the first and second pairs of opposed hook members, from their predetermined laterally spaced relationship further comprises:

two splines, one spline operably affixed to each of the opposed sides of the stem, the two splines extending substantially parallel to the longitudinal axis, in opposite directions beyond and away from the ends of the stem, each of the two splines having two ends; and one hook member of each of the first and second pairs of opposed hook members operably disposed on each spline end whereby each of the first and second pairs of opposed hook members is arranged in the predetermined laterally spaced relationship.

8. The spacer clip apparatus according to claim 7 wherein the means for substantially simultaneously deflecting the hook members of each of the first and second pairs of opposed hook members, from their predetermined lateral spaced relationship further comprises:

each of the two splines being affixed to the stem by webs extending outwardly from the stem at its ends, substantially perpendicularly to the longitudinal axis of the stem, so as to hold the splines in substantially parallel, spaced relationship to the stem; and each of the splines being fabricated of a resistively flexible material which will bend under the exertion of manual pressure, directed inwardly toward the stem, such that upon the exertion of squeezing pressure by an operator upon the splines, between the webs, the ends of the splines will deflect outward laterally away from the stem, facilitating release of, or fit onto, the first and second handles of the first inner and second outer needles, respectively.

9. The spacer clip apparatus according to claim 5 further comprising:

means for facilitating grasping of the spacer clip apparatus.

10. The spacer clip apparatus according to claim 9 wherein the splines are provided with sides facing outwardly away from the stem, the means for facilitating grasping of the spacer clip apparatus further comprising:

a plurality of reeded ridges operably disposed on the outward facing sides of the splines.

11. The spacer clip apparatus according to claim 10 wherein the plurality of reeded ridges are disposed on the outwardly facing sides of the splines in parallel, spaced relation to each other, each reeded ridge extending in a plane disposed substantially perpendicularly to the longitudinal axis of the stem.

* * * * *

UNITED STATES PATENT AND TRADEMARK OFFICE
CERTIFICATE OF CORRECTION

PATENT NO.   :   5,092,870
DATED        :   March 3, 1992
INVENTOR(S)  :   Mittermeier It is certified that error appears in the above-identified patent and that said Letters Patent is hereby corrected as shown below:

On title page, item [54], and col. 1, lines 1-2,
"SPACER CLIP FOR USE WITH A BIOPSY APPARATUS" should read instead -- SPACER CLIP FOR USE WITH BIOPSY NEEDLES --

Col. 7, line 10         after "needle" insert -- 11 --

Signed and Sealed this

Twenty-fourth Day of August, 1993

Attest:

BRUCE LEHMAN

Attesting Officer        Commissioner of Patents and Trademarks